United States Patent
Nakashima

(10) Patent No.: US 10,561,566 B2
(45) Date of Patent: Feb. 18, 2020

(54) WALKING ASSISTANCE APPARATUS AND WALKING TRAINING METHOD

(71) Applicant: TOYOTA JIDOSHA KABUSHIKI KAISHA, Toyota-shi (JP)

(72) Inventor: Issei Nakashima, Toyota (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 221 days.

(21) Appl. No.: 15/449,515

(22) Filed: Mar. 3, 2017

(65) Prior Publication Data

US 2017/0273852 A1 Sep. 28, 2017

(30) Foreign Application Priority Data

Mar. 23, 2016 (JP) .................................. 2016-058409

(51) Int. Cl.
*A61H 3/00* (2006.01)
*G09B 5/02* (2006.01)
(Continued)

(52) U.S. Cl.
CPC ................ *A61H 3/00* (2013.01); *A61F 2/60* (2013.01); *A61H 1/024* (2013.01); *A61H 1/0244* (2013.01); *A61H 1/0266* (2013.01); *A61H 3/008* (2013.01); *A61H 23/02* (2013.01); *A63B 21/00181* (2013.01); *A63B 22/0235* (2013.01); *A63B 24/0087* (2013.01); *G09B 5/02* (2013.01); *G09B 19/003* (2013.01); *G09B 19/0038* (2013.01);
(Continued)

(58) Field of Classification Search
CPC ...................................................... A61H 3/00
See application file for complete search history.

(56) References Cited

U.S. PATENT DOCUMENTS

| 5,121,747 A | 6/1992 | Andrews |
| 2004/0097330 A1 | 5/2004 | Edgerton et al. |
| 2013/0012852 A1 | 1/2013 | Imaida et al. |

FOREIGN PATENT DOCUMENTS

| EP | 1 595 522 A1 | 11/2005 |
| JP | 60-119949 A | 6/1985 |

(Continued)

OTHER PUBLICATIONS

R. Riener et al., "Robot-Supported Spasticity Evaluation," 9th Annual Conference of the International FES Society—Bournemouth, UK, www.control.ethz.ch, www.balgrist.ch, Sep. 2004, pp. 3.

(Continued)

*Primary Examiner* — Matthew W Schall
(74) *Attorney, Agent, or Firm* — Oblon, McClelland, Maier & Neustadt, L.L.P.

(57) ABSTRACT

A walking assistance apparatus includes stimulus applying means for applying a stimulus to a leg part on which a walking assistance apparatus is mounted and state detection means for detecting a supporting leg condition and a lifted leg condition of the leg part on which the walking assistance apparatus is mounted. The stimulus applying means applies a first stimulus to the leg part when the state detection means has detected that the leg part on which the walking assistance apparatus is mounted is in the lifted leg condition, and the stimulus applying means does not apply a stimulus to the leg part or applies a second stimulus that is weaker than the first stimulus when the state detection means has detected that the leg part on which the walking assistance apparatus is mounted is in the supporting leg condition.

4 Claims, 7 Drawing Sheets

(51) Int. Cl.
*A61H 1/02* (2006.01)
*A63B 21/00* (2006.01)
*G09B 19/00* (2006.01)
*A63B 24/00* (2006.01)
*A63B 22/02* (2006.01)
*A61F 2/60* (2006.01)
*A61H 23/02* (2006.01)
*A63B 69/00* (2006.01)
*A63B 71/06* (2006.01)
*A63B 71/00* (2006.01)

(52) U.S. Cl.
CPC ......... *A61H 2201/0173* (2013.01); *A61H 2201/0176* (2013.01); *A61H 2201/0192* (2013.01); *A61H 2201/1215* (2013.01); *A61H 2201/1261* (2013.01); *A61H 2201/14* (2013.01); *A61H 2201/1463* (2013.01); *A61H 2201/1481* (2013.01); *A61H 2201/163* (2013.01); *A61H 2201/164* (2013.01); *A61H 2201/165* (2013.01); *A61H 2201/1621* (2013.01); *A61H 2201/1676* (2013.01); *A61H 2201/5007* (2013.01); *A61H 2201/5043* (2013.01); *A61H 2201/5048* (2013.01); *A61H 2201/5061* (2013.01); *A61H 2201/5069* (2013.01); *A61H 2201/5071* (2013.01); *A61H 2201/5079* (2013.01); *A61H 2230/80* (2013.01); *A63B 21/4007* (2015.10); *A63B 21/4009* (2015.10); *A63B 21/4011* (2015.10); *A63B 69/0057* (2013.01); *A63B 71/0622* (2013.01); *A63B 2024/0093* (2013.01); *A63B 2071/0081* (2013.01); *A63B 2071/065* (2013.01); *A63B 2071/0625* (2013.01); *A63B 2071/0647* (2013.01); *A63B 2207/02* (2013.01); *A63B 2220/13* (2013.01); *A63B 2220/34* (2013.01); *A63B 2220/50* (2013.01); *A63B 2220/56* (2013.01); *A63B 2220/806* (2013.01); *A63B 2220/807* (2013.01); *A63B 2220/833* (2013.01); *A63B 2220/836* (2013.01); *A63B 2230/01* (2013.01)

(56) References Cited

FOREIGN PATENT DOCUMENTS

| | | |
|---|---|---|
| JP | 2007-520308 | 7/2007 |
| JP | 2009-60946 A | 3/2009 |
| JP | 2010-273748 A | 12/2010 |
| JP | 2012-95793 | 5/2012 |
| JP | 2013-138793 A | 7/2013 |
| KR | 10-1302364 B1 | 9/2013 |
| WO | WO 2005/087307 A2 | 9/2005 |
| WO | WO 2012/081107 A1 | 6/2012 |

OTHER PUBLICATIONS

Kazumi Kawahira et al., "Shindo Shigeki," Journal of Clinical Rehabilitation vol. 21 No. 6, 2012, pp. 3.

WALKING ASSISTANCE APPARATUS AND WALKING TRAINING METHOD

CROSS REFERENCE TO RERATED APPLICATIONS

This application is based upon and claims the benefit of priority from Japanese patent application No. 2016-058409, filed on Mar. 23, 2016, the disclosure of which is incorporated herein in its entirety by reference.

BACKGROUND

A walking assistance apparatus that is mounted on a leg part of a trainee and assists a walking operation of the trainee to perform walking training is known (see, for example, Japanese Unexamined Patent Application Publication No. 2012-095793).

In the meanwhile, in order to provide a trainee who is suffering from paralytic symptoms such as spasms or rigidity in his/her leg part with a treatment for relieving the paralysis of the leg part, the walking training needs to be temporarily or intermittently interrupted. This causes a problem that time required to complete the walking training increases, which time needs to be improved in view of efficiency. A treatment of applying stimuli to the leg part of the trainee on which the walking assistance apparatus is mounted has been performed to relieve the paralysis. When this treatment is simply performed on the leg part of the trainee during the walking training, however, a problem that the trainee loses his/her balance may occur.

SUMMARY

The present invention has been made in view of the aforementioned problems and aims to provide a walking assistance apparatus and a walking training method capable of performing a treatment for relieving the paralysis by which the walking of the trainee during the walking training is made stable while improving the efficiency of the walking training without interrupting the walking training.

One aspect of the present invention to accomplish the aforementioned object is a walking assistance apparatus configured to be mounted on a leg part of a trainee and assist a walking operation of repeating a supporting leg condition and a lifted leg condition of the leg part, the walking assistance apparatus including:

stimulus applying means for applying a stimulus to the leg part on which the walking assistance apparatus is mounted; and state detection means for detecting whether the leg part on which the walking assistance apparatus is mounted is in the supporting leg condition or the lifted leg condition, in which:

the stimulus applying means applies a first stimulus to the leg part when the state detection means has detected that the leg part on which the walking assistance apparatus is mounted is in the lifted leg condition, and the stimulus applying means does not apply a stimulus to the leg part or applies a second stimulus that is weaker than the first stimulus when the state detection means has detected that the leg part on which the walking assistance apparatus is mounted is in the supporting leg condition.

In this aspect, the stimulus applying means is drive means for rotatably moving a lower thigh frame relative to an upper thigh frame mounted on an upper thigh of the leg part of the trainee, the lower thigh frame being coupled to the upper thigh frame via a knee joint part and mounted on a lower thigh of the leg part, and the stimulus applying means may apply the stimulus to the leg part on which the walking assistance apparatus is mounted using vibrations generated by the driving of the knee joint part.

One aspect of the present invention to accomplish the aforementioned object may be a walking training method for mounting a walking assistance apparatus on a leg part of a trainee and assisting a walking operation of repeating a supporting leg condition and a lifted leg condition of the leg part, the walking training method including:

detecting the supporting leg condition and the lifted leg condition of the leg part on which the walking assistance apparatus is mounted;

applying a first stimulus to the leg part when it is detected that the leg part on which the walking assistance apparatus is mounted is in the lifted leg condition; and not applying a stimulus or applying a second stimulus that is weaker than the first stimulus to the leg part when it is detected that the leg part on which the walking assistance apparatus is mounted is in the supporting leg condition.

According to the present invention, it is possible to provide a walking assistance apparatus and a walking training method capable of performing a treatment for relieving the paralysis by which the walking of the trainee during the walking training is made stable while improving the efficiency of the walking training.

The above and other objects, features and advantages of the present invention will become more fully understood from the detailed description given hereinbelow and the accompanying drawings which are given by way of illustration only, and thus are not to be considered as limiting the present invention.

DESCRIPTION OF EMBODIMENTS

First Embodiment

Figure 1:
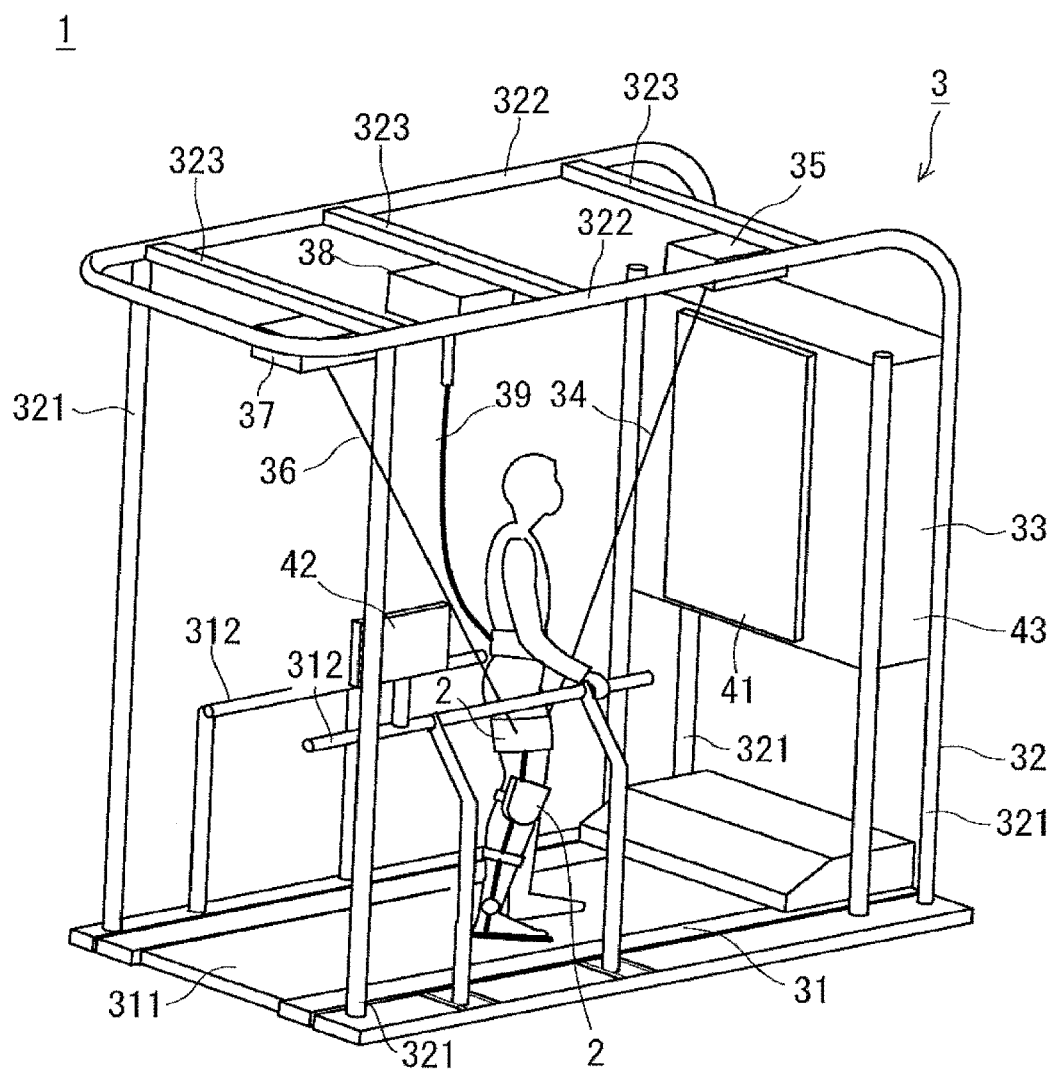
FIG. 1 is a perspective view showing a schematic configuration of a walking training system according to a first embodiment of the present invention.
Figure 2:
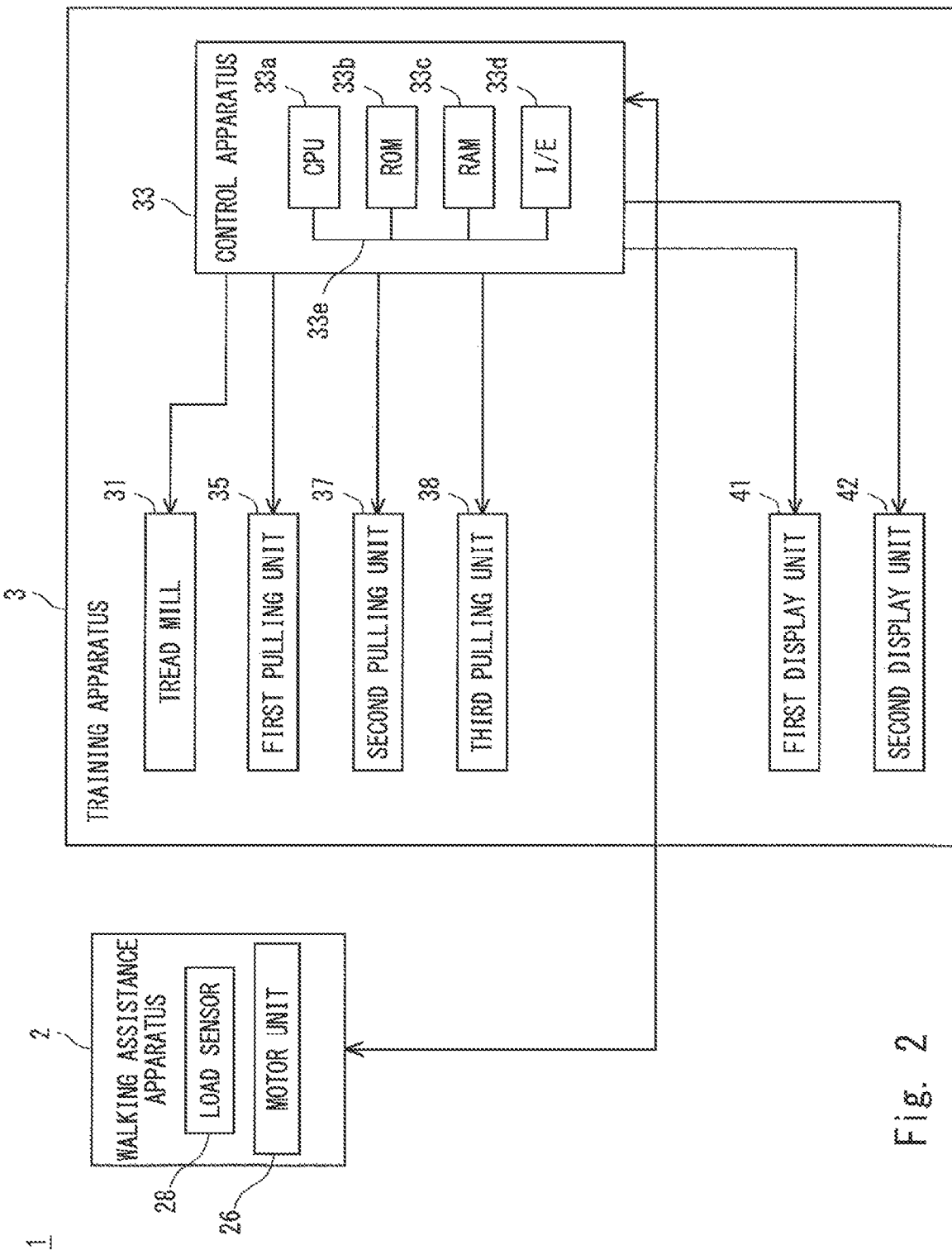
FIG. 2 is a block diagram showing a schematic system configuration of the walking training system according to the first embodiment of the present invention.

FIG. 1 is a perspective view showing a schematic configuration of a walking training system according to a first embodiment of the present invention. FIG. 2 is a block diagram showing a schematic system configuration of the walking training system according to the first embodiment of the present invention. A walking training system 1 according to the first embodiment is, for example, a device that performs walking training for a trainee (e.g., a patient suffering from hemiplegia due to a stroke). The walking training system 1 includes a walking assistance apparatus 2 mounted on a leg part of the trainee and a training apparatus 3 which performs the walking training for the trainee.

Figure 3:
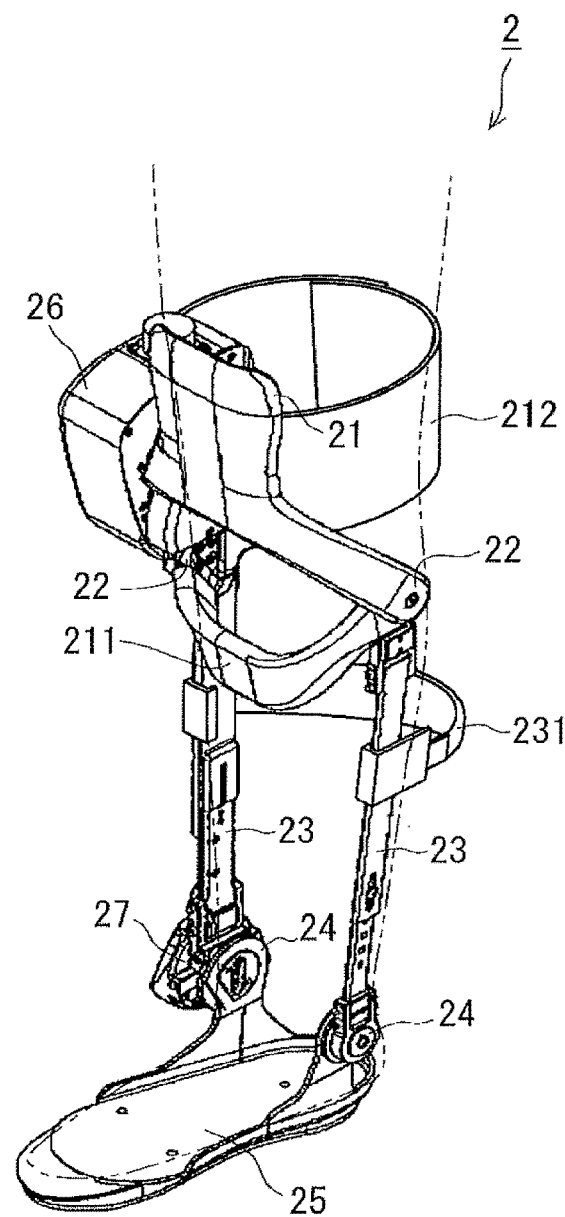
FIG. 3 is a perspective view showing a schematic configuration of a walking assistance apparatus according to the first embodiment of the present invention.

The walking assistance apparatus 2 according to the first embodiment is mounted, for example, on an affected leg of the trainee that performs walking training and assists trainee's walking (FIG. 3). The walking assistance apparatus 2 includes an upper thigh frame 21, a lower thigh frame 23 connected to the upper thigh frame 21 via a knee joint part 22, a sole frame 25 connected to the lower thigh frame 23 via an ankle joint part 24, a motor unit 26 that rotatably drives the knee joint part 22, and an adjustment mechanism 27 that adjusts a movable range of the ankle joint part 24. The structure of the walking assistance apparatus 2 is merely one example and the structure thereof is not limited to the one stated above. The walking assistance apparatus 2 may include, for example, a motor unit that rotatably drives the ankle joint part 24.

The upper thigh frame 21 is fixed to the upper thigh part of the leg part of the trainee and the lower thigh frame 23 is fixed to the lower thigh part of the leg part of the trainee. The upper thigh frame 21 is provided with, for example, an upper thigh equipment 212 to fix the upper thigh part.

The upper thigh frame 21 is provided with a first frame 211 which is formed in a horizontally long shape and extends in the horizontal direction so that the first frame 211 is connected to a wire 34 of a first pulling unit 35 described later. The lower thigh frame 23 is provided with a second frame 231 which is formed in a horizontally long shape and extends in the horizontal direction so that the second frame 231 is connected to a wire 36 of a second pulling unit 37 described later.

The sole frame 25 is provided with a load sensor 28. The load sensor 28 is, for example, a vertical load sensor that detects a vertical load applied to the sole of the sole frame 25. The load sensor 28 outputs a load value applied to the sole of the sole frame 25 that has been detected to a control apparatus 33.

The motor unit 26 is one specific example of drive means. The motor unit 26 assists the trainee's walking by rotatably driving the knee joint part 22 in accordance with the trainee's walking operation. The structure of the walking assistance apparatus 2 is merely one example and is not limited to the one stated above. A desired walking assistance apparatus that is mounted on the leg part of the trainee and is able to assist the trainee's walking can be applied.

The training apparatus 3 includes a tread mill 31, a frame body 32, a control apparatus 33, a first pulling unit 35, a second pulling unit 37, and a third pulling unit 38. The treadmill 31 rotates a ring-shaped belt 311. A pair of handrails 312 are provided on the respective sides of the tread mill 31 along the belt 311. The trainee stands on the belt 311, walks in accordance with the movement of the belt 311, and holds the handrails 312 provided on the respective sides of the tread mill 31 as necessary, to thereby perform the walking training.

The frame body 32 includes two pairs of column frames 321 which are installed on the tread mill 31, a pair of longitudinal frames 322 which are connected to the respective column frames 321 and extend in the longitudinal direction, and three horizontal frames 323 which are connected to the longitudinal frames 322 and extend in the horizontal direction. The configuration of the frame body 32 is not limited to the one described above. The frame body 32 may have any frame configuration as long as the frame body 32 can appropriately support the first pulling unit 35, the second pulling unit 37, and the third pulling unit 38 which will be described later to allow the first pulling unit 35, the second pulling unit 37, and the third pulling unit 38 to move.

The horizontal frame 323 on the front side of the training apparatus 3 is provided with the first pulling unit 35 that pulls the wire 34 to the upper side and the front side of the training apparatus 3. The horizontal frame 323 on the rear side of the training apparatus 3 is provided with the second pulling unit 37 that pulls the wire 36 to the upper side and the rear side of the training apparatus 3.

The first pulling unit 35 and the second pulling unit 37 include, for example, mechanisms which wind and rewind the wires 34 and 36, respectively, and motors which drive these mechanisms. One end of the wire 34 pulled by the first pulling unit 35 and one end of the wire 36 pulled by the second pulling unit 37 are connected to the walking assistance apparatus 2. The first pulling unit 35 pulls the walking assistance apparatus 2 to the upper side and the front side of the training apparatus 3 via the wire 34. The second pulling unit 37 pulls the walking assistance apparatus 2 to the upper side and the rear side of the training apparatus 3 via the wire 36. The first pulling unit 35 and the second pulling unit 37 control the pulling forces of the wires 34 and 36 by controlling drive torque of the motor.

Components in the vertically upward direction generated by the first pulling unit 35 and the second pulling unit 37 relieve the load of the walking assistance apparatus 2. Components in the horizontal direction of the pulling forces generated by the first pulling unit 35 and the second pulling unit 37 assist the starting of the movement of the leg part. Accordingly, it is possible to reduce a walking load of the trainee at the time of the walking training.

The third pulling unit 38 is provided in the middle horizontal frame 323 and pulls a wire 39 to the upper side of the training apparatus 3. One end of the wire 39 is connected, for example, to a belt which is attached to a part around a waist of the trainee. The third pulling unit 38 is composed of, for example, a mechanism for winding or unwinding the wire 39, and a motor for driving the mechanism. The third pulling unit 38 pulls the waist of the trainee upward through the wire 39. This structure can reduce the load due to the weight of the trainee.

A first display unit 41 for the trainee which displays information such as a training instruction, a training menu, and training information (walking speed, biological information and the like), a control apparatus 33, a power supply 43 and the like are provided on the front side of the frame body 32. The handrail 312 is provided with a second display unit 42 for a physical therapist that displays information such as a training instruction, a training menu, and training information. The first display unit 41 and the second display unit 42 are configured to be, for example, touch panels, and the trainee, the physical therapist or the like can input various items of information via the first display unit 41 and the second display unit 42. The first display unit 41 and the second display unit 42 are connected to the control apparatus 33.

The control apparatus 33 controls each of the pulling forces of the first pulling unit 35, the second pulling unit 37, and the third pulling unit 38, the driving of the tread mill 31, and the driving of the walking assistance apparatus 2. The control apparatus 33 has a hardware configuration mainly including, for example, a microcomputer which is formed of a central processing unit (CPU) 33a which performs an operating process, a control process or the like, a read only memory (ROM) 33b which stores an operation program performed by the CPU 33a, a control program, or the like, a random access memory (RAM) 33c which stores various items of data, an interface unit (I/F) 33d which performs input/output of signals to/from the outside, and the like. The CPU 33a, the ROM 33b, the RAM 33c, and the interface unit 33d are connected to one another via a data bus 33e.

In the meanwhile, in order to provide a trainee who is suffering from paralytic symptoms such as spasms or rigidity in his/her leg part with a treatment for relieving the paralysis of the leg part, the walking training needs to be temporarily or intermittently interrupted. This causes a problem that time required to complete the walking training increases, which time needs to be improved in view of the efficiency. If a treatment of applying stimuli to the leg part of the trainee is simply performed on the leg part of the trainee which is in the supporting leg condition (explained hereafter) during the walking training to relieve the paralysis, such a problem that the trainee loses his/her balance may occur.

On the other hand, in the first embodiment, the stimulus applied to the leg part when it is detected that the leg part on which the walking assistance apparatus 2 is mounted is in the supporting leg condition (explained hereafter) is smaller than the stimulus applied to the leg part when it is detected that the leg part on which the walking assistance apparatus 2 is mounted is in the lifted leg condition (explained hereafter).

It is therefore possible to apply stimuli to the leg part on which the walking assistance apparatus 2 is mounted during the walking training without interrupting the walking training, to thereby perform the treatment for relieving the paralysis while improving the training efficiency. Further, by applying normal or large stimuli to the leg part which is in the lifted leg condition, which is a condition in which the leg part does not support the weight of the trainee, the treatment for relieving the paralysis can be efficiently performed. Further, by applying no or small stimuli to the leg part which is in the supporting leg condition, which is a condition in which the leg part is supporting the weight of the trainee, the walking operation of the trainee can be made stable. That is, it is possible to perform the treatment for relieving the paralysis by which the walking of the trainee during the walking training is made stable while improving the efficiency of the walking training without interrupting the walking training.

When the walking assistance apparatus 2 detects that the leg part on which the walking assistance apparatus 2 is mounted is in the lifted leg condition, for example, the walking assistance apparatus 2 applies a first stimulus to the leg part. On the other hand, when the walking assistance apparatus detects that the leg part on which the walking assistance apparatus 2 is mounted is in the supporting leg condition, the walking assistance apparatus 2 does not apply any stimulus to the leg part. In this case, the walking assistance apparatus 2 applies the first stimulus to the leg part which is in the lifted leg condition, in which the leg part does not support the weight of the trainee, and does not apply any stimulus to the leg part which is in the supporting leg condition, which is a condition in which the leg part is supporting the weight of the trainee, whereby it is possible to perform the treatment for relieving the paralysis by which the walking of the trainee during the walking training is made stable. That is, it is possible to perform the treatment for relieving the paralysis by which the walking of the trainee during the walking training is made stable while improving the efficiency of the walking training without interrupting the walking training.

Figure 4:
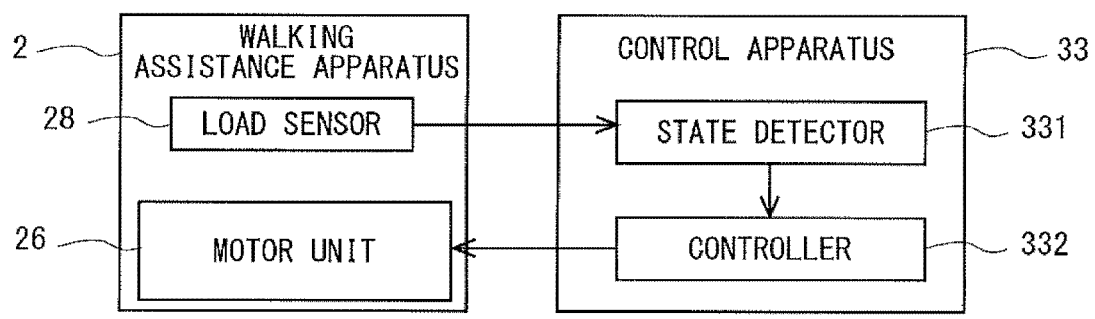
FIG. 4 is a block diagram showing a schematic system configuration of a control apparatus according to the first embodiment of the present invention.

FIG. 4 is a block diagram showing a schematic system configuration of the control apparatus according to the first embodiment. The control apparatus 33 according to the first embodiment includes a state detector 331 that detects whether the leg part of the trainee on which the walking assistance apparatus 2 is mounted is in the supporting leg condition or the lifted leg condition, and a controller 332 that controls the motor unit 26.

The state detector 331 is one specific example of state detection means. The state detector 331 detects whether the leg part is in the supporting leg condition or the lifted leg condition based on, for example, the load value output from the load sensor 28 provided in the sole frame 25 of the walking assistance apparatus 2. When a plurality of load sensors 28 are provided in the sole frame 25, the average of the load values output from the respective load sensors 28 may be set, for example, as the load value.

More specifically, when the load value output from the load sensor 28 is equal to or larger than a load threshold, the state detector 331 detects that the leg part on which the walking assistance apparatus 2 is mounted is in the supporting leg condition. On the other hand, when the load value output from the load sensor 28 is smaller than the load threshold, the state detector 331 detects that the leg part on which the walking assistance apparatus 2 is mounted is in the lifted leg condition. It is therefore possible to easily detect whether the leg part is in the supporting leg condition or the lifted leg condition using the load sensor 28 provided in the walking assistance apparatus 2.

The predetermined value stated above may be, for example, a load value when the leg part is in the supporting leg condition and the lifted leg condition measured by the load sensor 28 in advance before the walking training is started, and the predetermined value is set in the ROM 33b, the RAM 33c and the like. The state detector 331 outputs the result of the detection whether the leg part is in the supporting leg condition or the lifted leg condition to the controller 332.

The controller 332 controls the motor unit 26 of the walking assistance apparatus 2 according to the result of the detection sent from the state detector 331. The controller 332 transmits a knee angle command value indicating the knee joint angle to the motor unit 26 of the walking assistance apparatus 2. The motor unit 26 drives the knee joint part 22 in accordance with the knee angle command value sent from the controller 332.

When the controller 332 receives the result of the detection that the supporting leg condition has been detected from the state detector 331, the controller 332 generates a normal knee angle command value and outputs the generated value to the motor unit 26 of the walking assistance apparatus 2. In this case, the motor unit 26 normally drives the knee joint part 22 without generating vibrations in accordance with the normal knee angle command value. As stated above, no vibrational stimulus is applied to the leg part which is in the supporting leg condition, which is a condition in which the leg part is supporting the weight of the trainee, whereby it is possible to prevent a situation in which the walking by the trainee during the walking training becomes unstable.

Figure 5:
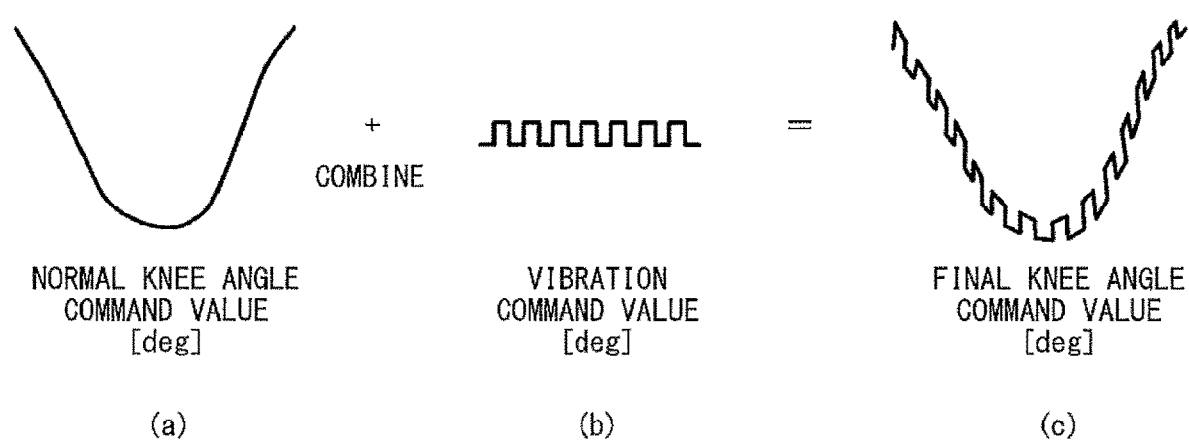
FIG. 5 is a diagram showing one example of a method of generating a final knee angle command value to generate vibrations.

On the other hand, when the controller 332 receives the result of the detection that the lifted leg condition has been detected from the state detector 331, the controller 332 generates, for example, a final knee angle command value (c) obtained by combining a normal knee angle command value (a) with a pulsed vibration command value (b) (FIG. 5) and outputs the generated value to the motor unit 26 of the walking assistance apparatus 2. The motor unit 26 vibrationally drives the knee joint part 22 in accordance with the final knee angle command value (c) from the controller 332. It is therefore possible to vibrate the walking assistance apparatus 2 and apply vibrational stimuli to the leg part on which the walking assistance apparatus 2 is mounted, to thereby perform the treatment for relieving the paralysis of the leg part. While the motor unit 26 is configured to vibrationally drive the knee joint part 22 in accordance with the final knee angle command value (c) from the controller 332, the configuration of the motor unit 26 is not limited thereto. The motor unit 26 may include a configuration, for example, in which it mechanically vibrates the knee joint part 22 (a configuration in which it eccentrically rotates the knee joint part 22).

As stated above, by applying the vibrational stimuli only to the leg part which is in the lifted leg condition, in which the leg part does not support the weight of the trainee, it is possible to perform the treatment for relieving the paralysis of the leg part without making the walking of the trainee during the walking training unstable.

Further, as stated above, the walking assistance apparatus 2 can be vibrated by generating the final knee angle command value by combining the normal knee angle command value with the pulsed vibration command value and generating the knee angle command value. In this case, there is no need to provide a special vibration generator or the like in the walking assistance apparatus 2, whereby it is possible to further reduce the size and the weight of the walking assistance apparatus 2.

A vibration generator (one specific example of stimulus applying means) may be provided in, for example, a predetermined part of the walking assistance apparatus 2 (e.g., the upper thigh frame 21, the knee joint part 22, the lower thigh frame 23, the ankle joint part 24, or the sole frame 25) to vibrate the walking assistance apparatus 2 more energetically. A plurality of vibration generators may be provided. When the controller 332 receives the result of the detection that the lifted leg condition has been detected from the state detector 331, the controller 332 controls the vibration generator to vibrate the vibration generator of the walking assistance apparatus 2. In this configuration, the vibration generator is provided near a paralyzed leg part where it is especially required to apply the stimuli, whereby it is possible to intensively apply the stimuli to the paralyzed part and to therefore perform the treatment for relieving the paralysis more efficiently.

Figure 6:
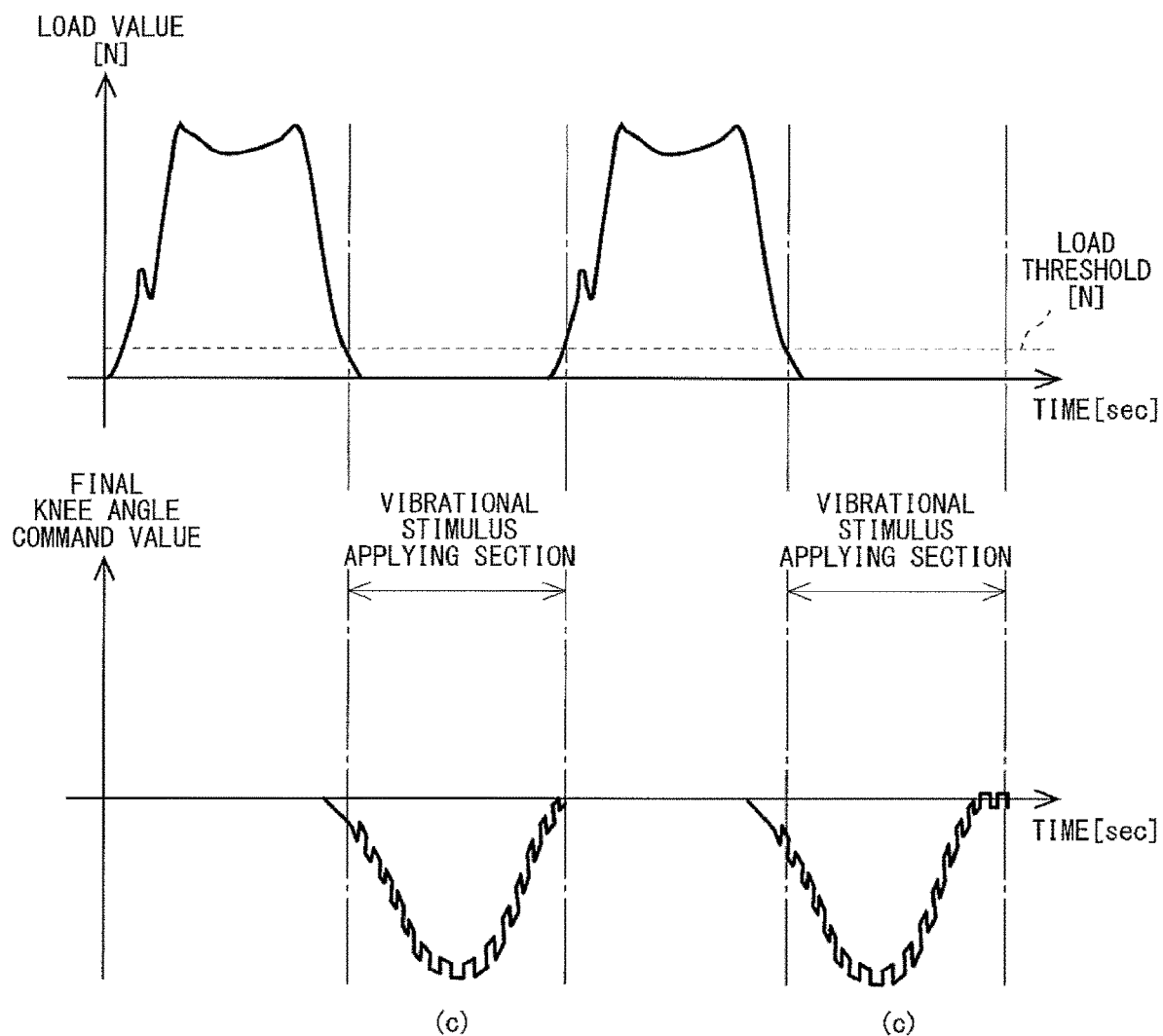
FIG. 6 is a diagram showing one example of a vibrational stimulus applying section in which vibrations are generated.

As shown in FIG. 6, when the load value output from the load sensor 28 becomes smaller than the load threshold, the state detector 331 detects that the leg part on which the walking assistance apparatus 2 is mounted is in the lifted leg condition and the controller 332 generates the final knee angle command value (c) in which the normal knee angle command value (a) is combined with the pulsed vibration command value (b) in a lifted leg period (vibrational stimulus applying section) and outputs the generated value to the motor unit 26 of the walking assistance apparatus 2. The motor unit 26 is able to vibrationally drive the knee joint part 22 in accordance with the final knee angle command value (c) from the controller 332 and to apply the stimuli of the vibrations (e.g., about 100 Hz) to the leg part on which the walking assistance apparatus 2 is mounted. It is therefore possible to relieve the paralytic symptoms of the trainee such as spasms or rigidity. In the first embodiment, the above vibrations can be adjusted, for example, within a range from 50 to 150 Hz by adjusting the vibration command value.

Figure 7:
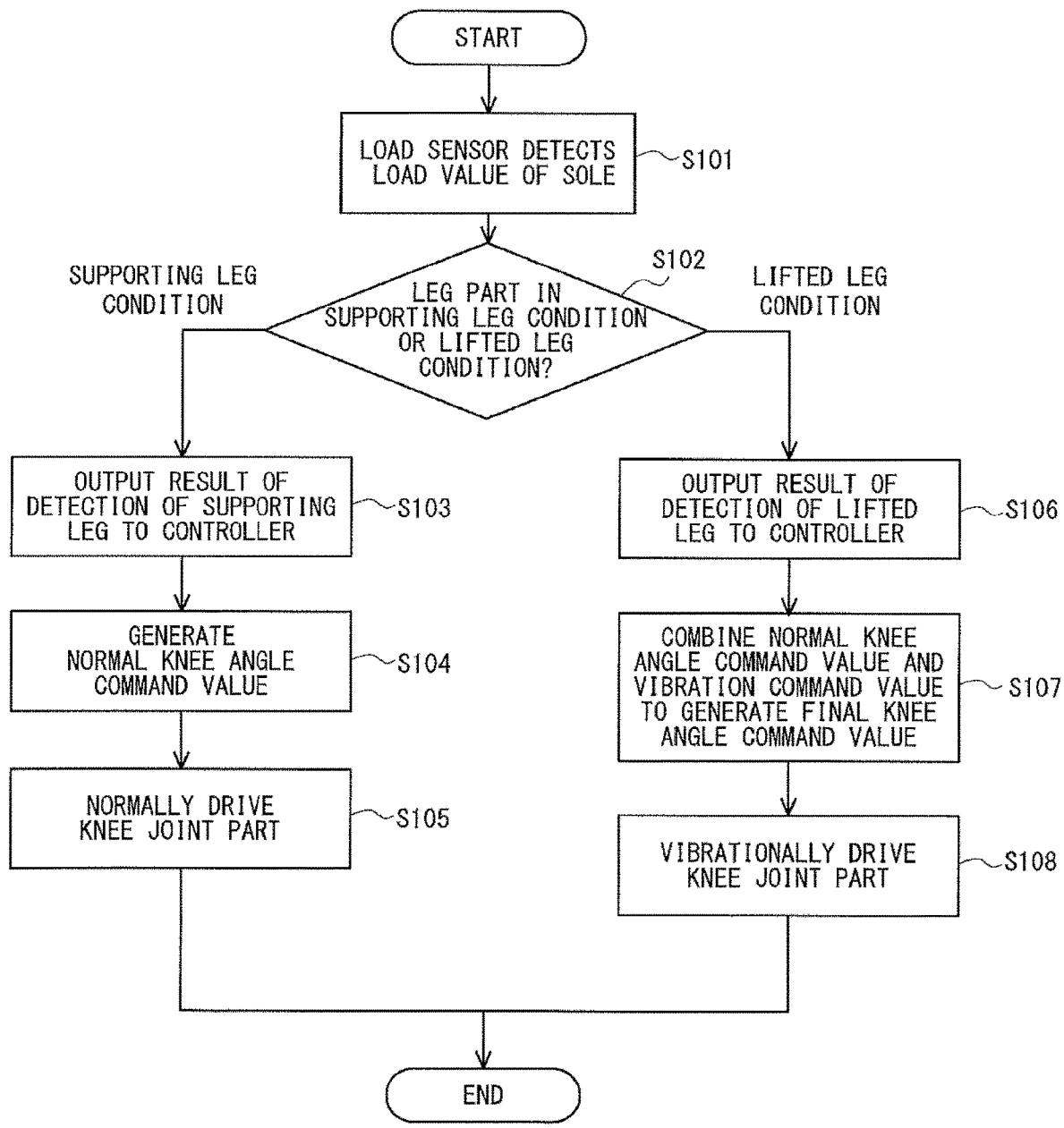
FIG. 7 is a flowchart showing a flow of a method of controlling the walking assistance apparatus according to the first embodiment of the present invention.

FIG. 7 is a flowchart showing a process flow of the walking training method according to this embodiment. The control flow shown in FIG. 7 is executed, for example, repeatedly at predetermined time intervals.

The load sensor 28 provided in the sole frame 25 of the walking assistance apparatus 2 detects the load value applied to the sole of the sole frame 25 and outputs the detected value to the control apparatus 33 (Step S101).

The state detector 331 of the control apparatus 33 detects whether the leg part on which the walking assistance apparatus 2 is mounted is in the supporting leg condition or the lifted leg condition based on the load value output from the load sensor 28 (Step S102).

When the state detector 331 of the control apparatus 33 detects that the leg part on which the walking assistance apparatus 2 is mounted is in the supporting leg condition (Step S102), the state detector 331 outputs the result of the detection that it has detected the supporting leg condition to the controller 332 (Step S103). Upon receiving the result of the detection that the supporting leg condition has been detected from the state detector 331, the controller 332 generates the normal knee angle command value and outputs the generated value to the motor unit 26 of the walking assistance apparatus 2 (Step S104). The motor unit 26 normally drives the knee joint part 22 in accordance with the normal knee angle command value from the controller 332 without generating vibrations (Step S105).

On the other hand, when the state detector 331 of the control apparatus 33 detects that the leg part on which the walking assistance apparatus 2 is mounted is in the lifted leg condition (Step S102), the state detector 331 outputs the result of the detection that it has detected the lifted leg condition to the controller 332 (Step S106).

When the controller 332 receives the result of the detection that the lifted leg condition has been detected from the state detector 331, the controller 332 generates the final knee angle command value obtained by combining the normal knee angle command value with the pulsed vibration command value and outputs the generated value to the motor unit 26 of the walking assistance apparatus 2 (Step S107). The motor unit 26 vibrationally drives the knee joint part 22 in accordance with the final knee angle command value from the controller 332 (Step S108).

Second Embodiment

In a second embodiment according to the present invention, when the walking assistance apparatus 2 detects that the leg part on which the walking assistance apparatus 2 is mounted is in the lifted leg condition, the walking assistance apparatus 2 applies a first stimulus whose value is set to a first stimulus value to the leg part. On the other hand, when the walking assistance apparatus 2 detects that the leg part on which the walking assistance apparatus 2 is mounted is in the supporting leg condition, the walking assistance apparatus 2 applies a second stimulus whose value is set to a second stimulus value which is smaller than the first stimulus value to the leg part.

In this case, a large stimulus is applied to the leg part which is in the lifted leg condition, which is a condition in which the leg part does not support the weight of the trainee, specifically for the purpose of performing the treatment for relieving the paralysis and a small stimulus that does not affect the walking operation is applied to the leg part which is in the supporting leg condition, which is a condition in which the leg part is supporting the weight of the trainee. It is therefore possible to constantly apply the stimuli to the leg part on which the walking assistance apparatus 2 is mounted during the walking training, whereby it is possible to efficiently perform the treatment for relieving the paralysis. In this case as well, a small stimulus is applied to the leg part which is in the supporting leg condition, which is a condition in which the leg part is supporting the weight of the trainee, whereby it is possible to perform the treatment for relieving the paralysis while making the walking operation by the trainee stable.

The first and second stimulus values stated above are set, for example, in the ROM 33b or the RAM 33c so that the trainee or the like can change the values that have been set. The trainee or the like changes the first and second stimulus values that have been set in consideration of the paralyzed state of the leg part.

More specifically, when the state of the paralysis of the leg part has relatively recovered and the walking operation is stable, the first and second stimulus values (the second stimulus value, in particular) are increased. It is therefore possible to apply stimuli to the leg part specifically for the purpose of performing the treatment for relieving the paralysis. On the other hand, when the state of the paralysis of the leg part has not recovered satisfactorily and the walking operation is still unstable, the first and second stimulus values (the second stimulus value, in particular) are decreased. It is therefore possible to apply stimuli to the leg part while giving a higher priority to the stability of the walking operation. As stated above, according to the second embodiment, by changing the first and second stimulus values that have been set depending on the state of the trainee such as the state of the paralysis of the leg part, it is possible to efficiently perform the treatment for relieving the paralysis while stabilizing the walking operation of the trainee during the walking training.

The present invention is not limited to the aforementioned embodiments and may be changed as appropriate without departing from the spirit of the present invention.

In the above embodiment, vibrational stimuli are applied to the leg part on which the walking assistance apparatus 2 is mounted by vibrating the walking assistance apparatus 2 to perform the treatment for relieving the paralysis of the leg part. However, the present invention is not limited to this case. Electrical or magnetic stimuli may be applied to the leg part on which the walking assistance apparatus 2 is mounted to perform the treatment for relieving the paralysis of the leg part.

In the above embodiment, when the walking assistance apparatus 2 includes the motor unit that rotatably drives the ankle joint part 24, the motor unit of the ankle joint part 24 may be controlled in a way similar to the control of the motor unit 26 of the knee joint part 22.

In the above embodiment, when the controller 332 of the control apparatus 33 receives the result of the detection that the lifted leg condition has been detected from the state detector 331, the controller 332 may control the first pulling unit 35 and the second pulling unit 37 and vibrate the wire 34 of the first pulling unit 35 and the wire 36 of the second pulling unit 37, to thereby vibrate the walking assistance apparatus 2.

While the state detector 331 of the control apparatus 33 detects whether the leg part is in the supporting leg condition or the lifted leg condition by comparing the load value output from the load sensor 28 provided in the sole frame 25 of the walking assistance apparatus 2 with the predetermined value in the above embodiments, the detection method performed by the state detector 331 is not limited to this case. The state detector 331 may calculate the center of gravity of the trainee based on the load value output from the load sensor 28 and detect whether the leg part is in the supporting leg condition or the lifted leg condition based on the center of gravity that has been calculated. The regions of the center of gravity when the leg part is in the supporting leg condition and the lifted leg condition are calculated, for example, in advance. Then the state detector 331 detects whether the leg part is in the supporting leg condition or the lifted leg condition by detecting in which region the center of gravity of the trainee calculated based on the load value output from the load sensor 28 falls.

The state detector 331 of the control apparatus 33 may detect whether the leg part on which the walking assistance apparatus 2 is mounted is in the supporting leg condition or the lifted leg condition based on the time variation of the angle of the knee joint part detected by the angle sensor provided in the knee joint part of the walking assistance apparatus 2. More specifically, the state detector 331 detects whether the leg part is in the supporting leg condition or the lifted leg condition when it determines that the detected angle has entered a changing range corresponding to the supporting leg condition or the lifted leg condition based on the time variation of the angle of the knee joint part detected by the angle sensor.

The state detector 331 of the control apparatus 33 may detect whether the leg part on which the walking assistance apparatus 2 is mounted is in the supporting leg condition or the lifted leg condition based on the user's walking period calculated from the moving speed of the belt 311 of the tread mill 31. The relation between the walking period and the moving speed of the belt 311 of the tread mill 31 can be experimentally obtained in advance (e.g., the walking period is a monotone decreasing function with the moving speed of the belt 311 of the tread mill 31 as a variable). The above method of detecting the supporting leg condition or the lifted leg condition is merely one example. The detection method is not limited to the one described above and any detection method may be applied.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A walking assistance apparatus configured to be mounted on a leg part of a trainee and assist a walking operation of repeating a supporting leg condition and a lifted leg condition of the leg part, the walking assistance apparatus comprising:
    a stimulus applying unit that applies a stimulus to the leg part; and
    a state detector that detects whether the leg part is in the supporting leg condition or the lifted leg condition, wherein
    the stimulus applying unit applies a first stimulus to the leg part when the state detector has detected that the leg part is in the lifted leg condition, and
    the stimulus applying unit does not apply a stimulus to the leg part or applies a second stimulus that is weaker than the first stimulus when the state detector has detected that the leg part is in the supporting leg condition.

2. The walking assistance apparatus according to claim 1, wherein:
    the stimulus applying unit is a driver for rotatably moving a lower thigh frame relative to an upper thigh frame mounted on an upper thigh of the leg part of the trainee, the lower thigh frame being coupled to the upper thigh frame via a knee joint part and mounted on a lower thigh of the leg part, and the stimulus applying unit applies the stimulus to the leg part using vibrations generated by the driving of the knee joint part.

3. A walking training method for mounting a walking assistance apparatus on a leg part of a trainee and assisting a walking operation of repeating a supporting leg condition and a lifted leg condition of the leg part, the walking training method comprising:

detecting the supporting leg condition and the lifted leg condition of the leg part;

applying a first stimulus to the leg part when it is detected that the leg part is in the lifted leg condition; and not applying a stimulus or applying a second stimulus that is weaker than the first stimulus to the leg part when it is detected that the leg part on which the walking assistance apparatus is mounted is in the supporting leg condition.

4. The walking assistance apparatus according to claim 1, wherein:

the stimulus applying unit is a vibration generator that applies a vibration to the leg part based on an output of the state detector.

* * * * *